United States Patent [19]

Duggan

[11] Patent Number: 4,852,189
[45] Date of Patent: Aug. 1, 1989

[54] HEADBAND STRUCTURE

[76] Inventor: Charles M. Duggan, 3120 Earhart Rd., Ann Arbor, Mich. 48105

[21] Appl. No.: 234,554

[22] Filed: Aug. 22, 1988

[51] Int. Cl.[4] .......................... A61F 9/00; G02C 3/02
[52] U.S. Cl. .................................. 2/452; 2/DIG. 11; 2/454; 2/11; 2/15; 2/13
[58] Field of Search .................. 2/207, DIG. 11, 452, 2/454

[56] References Cited

U.S. PATENT DOCUMENTS

| | | | |
|---|---|---|---|
| 4,393,519 | 7/1983 | Nicastro | 2/DIG. 11 X |
| 4,520,510 | 12/1983 | Daigle | 2/207 X |
| 4,616,367 | 10/1986 | Jean, Jr. et al. | 2/DIG. 11 X |
| 4,712,254 | 12/1987 | Daigle | 2/DIG. 11 X |

*Primary Examiner*—Werner H. Schroeder
*Assistant Examiner*—Jeanette E. Chapman
*Attorney, Agent, or Firm*—Bertram F. Claeboe

[57] ABSTRACT

The present invention is directed particularly to a headband structure which includes a moisture absorptive member for encircling a human head in embracement with the brow thereof, the head encircling member taking various forms exemplified by a bandanna or an expansible or stretchable element constructed of terrycloth or cheesecloth having elastic means associated therewith. Further comprising the headband structrure of this invention is a preformed thermoplastic film-like eyeglass or vision member which is readily invertible by the wearer from an active line of sight position to an inactive out of line of sight position, or conversely, through the use of means effecting cooperative releasable engagement between the head encircling member and the eyeglass or vision member.

1 Claim, 1 Drawing Sheet

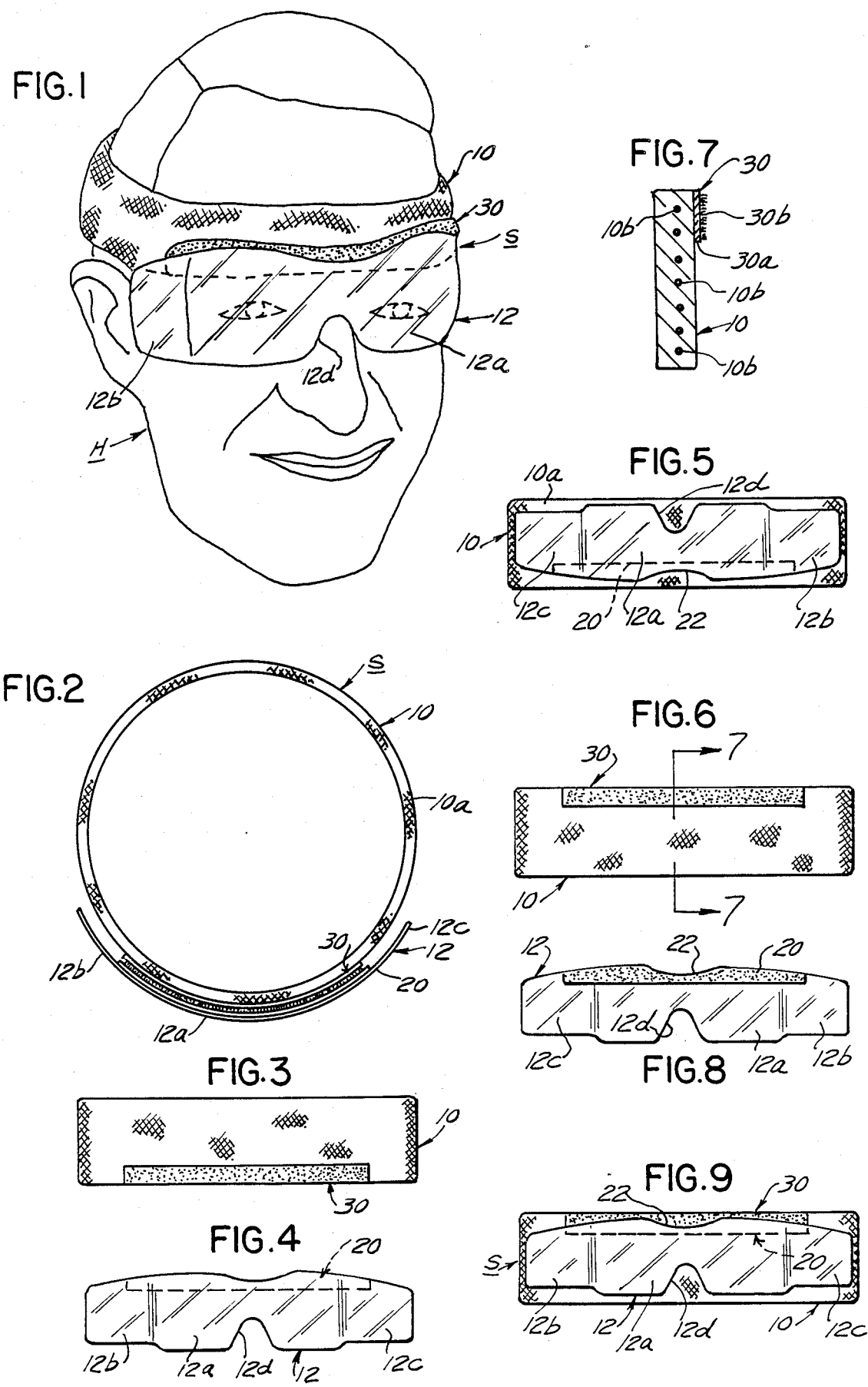

HEADBAND STRUCTURE

BACKGROUND OF THE INVENTION

It is known in the art to which this invention pertains to provide for the comfort and convenience of the wearer a combination of eyeglasses and headband, achieving thereby an integration of the prime function of each element of the composite structure. Various approaches have been taken toward accomplishment of this desirable objective, and in one device of which applicant is aware a conventional pair of spectacles adhesively mounts along the inner surface of the top cross frame members an elongated block of sponge-like material contoured for conforming engagement with the brow of the wearer of the spectacles. Another structure known to the art relates to goggles utilizing a nylon backing supporting a pair of lenses, the nylon backing having secured thereto a plurality of strips of hook and pile material to achieve adjustability of the structure. Hook tape has also been employed in another known arrangement as a part of a head encircling plastic band to support by depending loops a pair of conventional spectacles. It is further a part of the prior art of which applicant has knowledge to provide adjustability of headband-supported eyeglasses to positions into and out of the line of sight of the wearer, and in this same arrangement cooperating self-engaging strips are employed for circumferential adjustment of the headband and also vertical positioning of the eyeglasses relative to the headband.

DESCRIPTION OF THE PREFERRED EMBODIMENT

Characterizing features of the instant invention forming no part of known art are utilization of a universal size moisture absorptive headband constructed of known fabric materials requiring no substantial modification thereto for selective cooperable engagability with a preformed readily invertible frameless eyeglass member providing substantially wraparound eye protection against harmful sun ray infiltration or the intrusion of foreign substances or materials. More particularly, applicant's inventive contribution to the art is directed to a headband structure comprised of a perspiration absorptive member for encircling a human head in embracement with the brow or forehead, the head encircling member taking various forms exemplified by a bandanna or an expansible or stretchable element constructed of terrycloth or cheesecloth having elastic means associated therewith. Further comprising the headband structure of this invention is a thermoplastic film-like preformed eyeglass or vision member which is readily invertible by the wearer from an active line of sight position to an inactive out of line of sight position or conversely, through the use of means effecting cooperative releasable engagement between the head encircling member and eyeglass or vision member.

BRIEF DESCRIPTION OF THE DRAWINGS

FIG. 1 is a perspective view of the headband structure of this invention positioned on the head of a wearer;

FIG. 2 is a top plan view of the instant headband structure;

FIG. 3 is a front view of one form of perspiration or moisture absorptive member;

FIG. 4 is a front view of a preferred form of eyeglass on vision member;

FIG. 5 is a front view showing the headband structure with the eyeglass member in an inverted position or out of line of sight usage;

FIG. 6 is a front view showing the head encircling member of FIG. 3 in an inverted position;

FIG. 7 is a vertical sectional view taken substantially along the line 7—7 of FIG. 6;

FIG. 8 is a view similar to FIG. 4, but showing the inner surface of the eyeglass member of this invention with fastening means exposed; and FIG. 9 is a front view showing the members of FIGS. 6 and 8 in an assembled condition of active usage.

DESCRIPTION OF THE PREFERRED EMBODIMENT

Referring now first to FIG. 1 of the drawings, headband structure designated in its entirety by the legend S is shown in an active or line of sight position upon head H of a wearer in encircling embracement therewith. Structure S of this invention, as appears also in FIGS. 2, 3 and 4, comprises in combination a perspiration or moisture absorptive member 10 and preformed thermoplastic film-like eyeglass or vision member 12 in cooperative releasable engagement. The perspiration absorptive member 10 may be provided by a bandanna, which is generally defined as a large figured handkerchief, and in this event would normally be tied or knotted at the rear of the wearer's head H. More preferably, the member 10 takes the form of a stretchable or expansible fabric material exemplified by terrycloth or cheesecloth. Terrycloth is generally considered to be an absorbent fabric presenting a mass of uncut loops which forms the pile, while cheesecloth is defined as a very light unsized cotton gauze.

The woven character of the perspiration absorptive member 10 is denoted at 10a in FIG. 2, and in order to impart stretchability to the number 10 elastic bands or threads 10b are provided therein, as is shown in FIG. 7. The member 10, on occasion generically referred to in the art as "sweat band", is fabricated for use as a continuous body of generally circular shape, and is normally universally sized for both adults and children. Various decorative fabrics may be employed, and different indicia woven therein. Pouches may be provided to receive a key, pills or the like.

The thermoplastic film-like eyeglass or vision member 12, as appears best in FIGS. 1 and 2, is preferably of generally wraparound configuration so as to provide effective eye protection against harmful sun ray infiltration or the intrusion of foreign objects or substances. The rimless member 12 is accordingly shaped during the manufacturing process to generally confirm to the wearer's forehead or brow and a portion of the temple area, and as thus preformed includes a main central body portion 12a and a pair of rearwardly directed tab or wing portions 12b and 12c. As appears in FIGS. 1 and 4, the central body portion 12a may be notched or cut away as at 12d to accomodate the bridge portion of the nose of the wearer. It is to be noted that the eyeglass member 12 of this invention is not only rimless, but is free of temple pieces which are an inconvenience and often an ear irritant.

The eyeglass member 12 is preferably constructed of polyvinyl chloride or other synthetic thermoplastic polymers, exemplified by nylons, fluorocarbons, linear polyethylene, polyurethane prepolymer, polystyrene, polypropylene, or cellulosic or acrylic resins. The ultimate application of the headband structure S of the instant invention will of course determine the thickness of the eyeglass member 12, and also whether or not the member 12 is tinted and the degree of tinting. To illustrate, the eyeglass or vision member 12 may function in the nature of industrial safety glasses or as a face shield for motorcyclists or skiers, and thus would be of commensurate thickness and may not in all cases require tinting. However, for conventional sunglass applications, a thickness of about 2 mils for the eyeglass member 12 is exemplary, and a degree of tinting to generally exclude or filter beta rays of the UV spectrum is ordinarily sufficient for most applications.

The mode of effecting cooperative releasable engagement between the perspiration absorptive member 10 and the thermoplastic film-like eyeglass member 12 is through the use of at least one composite strip element of a cooperative pair of said elements identified in the trade by the "Velcro" trademark. As is known to the art, a cooperative pair of composite strip or pad elements of this character comprises pile and hook material providing the cooperative pair, formed in each case from a backing of a dimensionally stable woven nylon fabric. In the case of the pile material, the backing has on one side thereof a large plurality of tiny, upstanding loops of very fine thread or other filamentary material, this side being the pole side. The hook material, on the other hand, generally utilizes the same type of backing as the pile material and has a plurality of tiny hooks extending outwardly from one side of the backing, this side being the hook side. This combination of pile and hook material known commercially by the "Velcro" trademark is also referred to as hook tape.

As utilized as a part of the instant invention, the broadest application involving employment of the general hook tape concept is the disposition by any suitable means of a strip or pad of hook material upon the inner upper surface of the thermoplastic eyeglass member, the texture or construction of the perspiration absorptive member or headband effectively functioning in the nature of pile material exemplified by terrycloth. This is broadly shown in FIG. 8 of the drawings, wherein like numerals from FIG. 4 have been applied. Viewing the inner surface of the eyeglass number 12 as in FIG. 8, the upper marginal portion thereof mounts by adhesive means or the like a longitudinally or horizontally extending strip or pad 20 of hook material exposing the hook side thereof. The strip 20 is coextensive with the width of central body portion 12c of the eyeglass member 12, and preferably terminates inwardly of opposite ends of the tab or wing portions 12b and 12c of eyeglass member 12. Primarily for aesthetic and weight reduction reasons, eyeglass member 12 and hook material strip 20 thereon may be inwardly notched or grooved as at 22.

The eyeglass member 12 of FIG. 8, with strip 20 of hook material adhesively or otherwise secured thereto through the nylon backing support portion (not shown), is particularly well suited for association with a perspiration absorptive member 10 presenting a pile surface for cooperative releasable engagement with hook material strip 20. Terrycloth is especially well suited for this purpose, presenting a large plurality of tiny, upstanding loops of relatively fine thread in the manner of the pile material portion of hook tape marketed under the "Velcro" trademark. This is shown generally in FIG. 5, wherein the legend 10a referring in FIG. 2 to woven material serves to also identify in FIG. 5 a pile material surface having the capability of effecting releasable engagement with strip 20 of hook material adhesively or otherwise affixed to inner upper portion of eyeglass or vision member 12.

A significant feature of the instant invention, as noted hereinabove, is the ready invertibility or transposition of the eyeglass member 12 from an active or line of sight position to an inactive or out of line of sight position, and in both positions being in cooperative releasable engagement with the perspiration absorptive member or headband 10. This is also clearly illustrated in FIG. 5, and it may be noted therefrom when brief reference is also made to FIG. 1, inversion of the eyeglass member 12 and transposition thereof to an inactive or out of line of sight position merely requires a person's one hand to effect the detachment and a relatively simple 180° rotation of inversion of the eyeglass member 12 and attached hook material strip 20 to the inactive position of FIG. 5 with the strip 20 adherent to the fabric or loop material 10a of the headband 10. Loss of eyeglasses, their insertion into a case or garment pocket, and other inconveniences and disadvantages are effectively avoided by the eyeglass structure S of this invention.

In the event that the headband or moisture absorptive member 10 is smooth-surfaced and to this extent not readily engagable with hook material on the eyeglass member as described, or should it be desired to assure even more firm engagement between the eyeglass member 12 and a fabric-type headband 10, a pile material strip or pad may be attached in any suitable manner to the outer surface of the moisture absorptive member 10. Pile material preferably in strip form is identified in the drawings by the numeral 30, and as earlier noted and as also is shown in FIG. 7, pile material strip 30 comprises a backing 30a of woven nylon fabric or the equivalent thereof and on one side of said backing a large plurality of tiny, upstanding loops 30b of very fine thread or other filamentary material. This side is the pile side, and as previously noted, the combination of pile and hook material is known commercially under the "Velcro" trademark and is also referred to as hook tape.

The pile material strip 30 is attached to the headband or moisture absorptive member 10 along the outer lower portion thereof by sewing, adhesive means, or in any other suitable manner. Ready effective engagement and disengagement between hook strip 20 on rimless eyeglass member 12 and pile strip 30 on headband 10 are made in a manner believed now readily apparent, and all deficiencies of known prior art structures are herein effectively overcome by proceeding in the manner above described.

Various changes and modifications to the instant invention have been noted herein, and these and other variations may of course be effected without departing from the spirit of the invention or the scope of the subjoined claims.

I claim:

1. In combination with a continuous elastic headband having moisture absorptive properties and textured to present a larger plurality of upstanding fibrous loops, the improvement which compresses a rimless relative thin one-piece preformed flexible thermoplastic eyeglass member of generally wraparound configuration having a central body portion and integral rearwardly directed tapered wing portions to substantially entirely shield the eyes from sun rays and the intrusion of foreign objects, and means adhesively secured to the body and wing portions of said eyeglass member along the upper inner marginal portions thereof and presenting fibrous hooks outstanding therefrom for cooperative releasable engagement with the upstanding loops of the textured continuous elastic headband along the outer exposed surface thereof, said eyeglass member thereby being readily invertible by rotation through an angle of about 180 degrees from an active line of sight position on said headband depending downwardly thereon to an active out of line sight position on said headband extending upwardly thereon in releasable engagement therewith.

* * * * *